United States Patent
Talish

(10) Patent No.: US 6,322,527 B1
(45) Date of Patent: Nov. 27, 2001

(54) APPARATUS FOR ULTRASONIC BONE TREATMENT

(75) Inventor: Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/420,403

(22) Filed: Oct. 18, 1999

Related U.S. Application Data

(63) Continuation of application No. PCT/US98/07531, filed on Apr. 16, 1998.
(60) Provisional application No. 60/044,709, filed on Apr. 18, 1997.

(51) Int. Cl.[7] ................................................ A61B 17/56
(52) U.S. Cl. .............................. 601/2; 310/316; 310/348; 607/51
(58) Field of Search ......................... 601/2, 97; 310/316, 310/345, 348; 607/52, 50, 31; 600/439; 602/2; 439/909

(56) References Cited

U.S. PATENT DOCUMENTS

| | | |
|---|---|---|
| 4,530,360 | 7/1985 | Duarte . |
| 5,003,965 | 4/1991 | Talish et al. . |
| 5,186,162 | 2/1993 | Talish et al. . |
| 5,211,160 | 5/1993 | Talish et al. . |
| 5,556,372 | * 9/1996 | Talish et al. ............................. 601/2 |
| 5,755,746 | * 5/1998 | Lifshey et al. ......................... 607/50 |
| 5,762,616 | * 12/1999 | Talish ...................................... 601/2 |
| 5,997,490 | * 12/1999 | McLeod et al. ....................... 601/97 |

FOREIGN PATENT DOCUMENTS

WO 96/25888  3/1995  (WO) .
WO 96/25112  8/1995  (WO) .

* cited by examiner

Primary Examiner—Marvin M. Lateef
Assistant Examiner—Eleni Mantis Mercader
(74) Attorney, Agent, or Firm—Bruce D. Gray; Kilpatrick Stockton LLP

(57) ABSTRACT

The apparatus is used for therapeutically treating injuries using ultrasound. The present invention may include a therapeutic ultrasonic composite comprising a transducer and an integrated circuit unit positioned adjacent the transducer. The therapeutic ultrasonic composite also includes signal generation circuitry, housed on the integrated circuit unit, for generating a driving signal for the transducer, and a driving interface between the signal generation circuitry and the transducer. In operation, driving signals generated by the signal generation circuitry are transmitted to the transducer by the interface, thereby driving the transducer for the creation of therapeutic ultrasound.

23 Claims, 7 Drawing Sheets

APPARATUS FOR ULTRASONIC BONE TREATMENT

This application is a continuation of PCT/US98/07531 which is a provisional application of 60/044,709 filed Apr. 18, 1997.

BACKGROUND OF THE INVENTION

1. Field of the Invention

The present invention relates to an apparatus for therapeutically treating injuries using ultrasound. More particularly, the present invention relates to an apparatus which utilizes a portable signal generator and transducer for treating bone injuries or a variety of musculoskeletal injuries and/or problems.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte ("Duarte") describes a basic therapeutic technique and apparatus for applying ultrasonic pulses from an ultrasonic applicator placed on the skin at a location adjacent a bone injury. Duarte gives a range of R-F signals for creating the ultrasound, ultrasound power density levels, a range of duration for each ultrasonic pulse, and a range of ultrasonic pulse frequencies. The length of daily treatment is also described. The applicator described in the '360 patent has a plastic tube which serves as a grip for the operator, an R-F plug attached to the plastic tube for connection to an R-F source, and internal cabling connected to an ultrasonic transducer. To apply the ultrasound pulses during treatment an operator must manually hold the applicator in place until the treatment is complete. As a result, the patient is, in effect, immobilized during treatment. The longer the treatment period, the more the patient is inconvenienced.

In general, an ultrasound carrier frequency between 250 kHz and 10 MHz coupled with a relatively low-frequency modulating signal (e.g. 5 Hz to 10 kHz) and low intensity acoustic signal (e.g. less than 100 milliwatts/cm$^2$) aids, and will be effective in the wound-healing method and apparatus described above.

U.S. Pat. Nos. 5,003,965 and 5,186,162 both to Talish and Lifshey ("Talish '965" and "Talish '162", respectively) describe an ultrasonic delivery system where the R-F generator and transducer are both part of a modular applicator unit that is placed at the skin location. The signals controlling the duration of ultrasonic pulses and the pulse repetition frequency are generated apart from the applicator unit. Talish '965 and Talish '162 also describe fixture apparatus for attaching the applicator unit so that the operative surface is adjacent the skin location. In Talish '965 and Talish '162, the skin is surrounded by a cast, while in U.S. Pat. No. 5,211,160 to Talish and Lifshey ("Talish '160") fixture apparatus is described for mounting on uncovered body parts (i.e.,, without a cast or other medical wrapping). Talish '160 also describes various improvements to the applicator unit.

Duarte, Talish '965, Talish '162, and Talish '160, are all incorporated into this application by reference.

While the systems described in these patents relate to therapeutic methods and apparatus for ultrasonically treating injured bone, they do not disclose a self-contained signal. generator and transducer which permits maximum patient mobility during treatment. Therefore, a need exists for apparatus which optimizes patient mobility during therapeutic ultrasonic treatment.

SUMMARY OF THE INVENTION

The ultrasonic treatment apparatus of the present invention is used for therapeutically treating injuries using ultrasound. The apparatus includes an ultrasonic treatment composite having a signal generator which provides excitation signals for an ultrasonic transducer within the composite. The portable composite is constructed to be worn by the patient adjacent the treatment site, and provides treatment timer control circuitry. The composite may have a power interface for an external power supply, and a control interface, which appropriately activates the composite components in order to provide daily ultrasonic treatment. (Alternatively, the composite may have an integral power supply.) In operation, the composite is positioned with the transducer adjacent the external skin location corresponding to the injury and excited for a predetermined period of time.

Thus, the present invention may include a therapeutic ultrasonic composite comprising a transducer and an integrated circuit unit positioned adjacent the transducer. The therapeutic ultrasonic composite also includes signal generation circuitry, housed on the integrated circuit unit, for generating a driving signal for the transducer, and a driving interface between the signal generation circuitry and the transducer. In operation, driving signals generated by the signal generation circuitry are transmitted to the transducer by the interface, thereby driving the transducer for the creation of therapeutic ultrasound.

Preferably, the composite has a integrated circuit unit ("ICU") that is positioned adjacent a transducer, the ICU supporting the signal generator circuitry for providing excitation signals to the transducer. A control interface on the ICU can support a data link between the signal generator circuitry and external treatment control circuitry. When the data link is made across the control interface, the external treatment control circuitry provides appropriate control information to the signal generator circuitry, thus activating the therapeutic ultrasound treatment for a period of time.

In a preferred embodiment of the present invention, the ICU is a separate silicon based chip that is mounted to the non-operative surface (back surface) of a ceramic piezoelectric transducer wafer. The ICU has external leads that interface with receptors on the transducer, thus providing an electronic link so that driving signals created by the signal generator circuitry on the chip may drive the transducer. In an alternative preferred embodiment, the ICU is incorporated into the back side of the ceramic transducer wafer, which provides the substrate for the signal generator circuitry. In such an alternative embodiment, the electronic link between the signal generator circuitry and the transducer would be internal to the ceramic wafer.

Thus, an alternative preferred embodiment of the present invention includes a therapeutic ultrasonic composite comprising a transducer formed by a portion of a piezo-electric substrate, the transducer having an operative surface for the emission of therapeutic ultrasound. An integrated circuit is formed in a portion of the piezoelectric substrate, the integrated circuit having signal generation circuitry for generating a driving signal for the transducer. A driving interface is formed within the substrate between the signal generation circuitry and the transducer and, in operation, driving signals generated by the signal generation circuitry are transmitted to the transducer by the interface, thereby driving the transducer for the creation of therapeutic ultrasound at the operative surface.

The present invention also includes a system for providing therapeutic ultrasonic therapy comprising an ultrasonic treatment composite having an integrated circuit containing signal generation circuitry positioned adjacent and interfacing electronically with a transducer. The signal generation circuitry is configured to provide driving signals to the transducer via the interface for the generation of therapeutic ultrasound. An external treatment control circuitry separate from the composite is provided, and configured to generate control signals for the integrated circuit. A control interface between the external treatment control circuitry and the integrated circuit is included for transmitting the control signals generated by the external treatment control circuitry to the integrated circuit.

The signal generator circuitry preferably includes an R-F oscillator and modulator that interface with a driver, and a timer that activates and de-activates the signal generator circuitry. External treatment control circuitry serves to set the timer for an appropriate treatment interval when a data link is made across the control interface. The external treatment control circuitry can be comprised of a processor that generates a control signal for setting the timer. The control signals sent to the timer may be generated by the processor using data that is stored in memory for the particular patient, or may be generated by data that is entered into the processor by a keypad.

The external treatment control circuitry, for example, may be combined within a portable control unit that is prescribed to the patient along with the ultrasonic treatment composite. The control unit would be pre-programmed based on the treatment required for the particular patient. The patient would complete the data link between the control unit and the control interface of the ICTJ, and then activate the control unit. Control signals from the control unit would be generated and transmitted to the timer of the signal generator circuitry, thus activating the circuitry and delivering ultrasonic treatment for the prescribed time period.

Alternatively, the external treatment control circuitry may be remote from the patient, and the data link with the ICU may be provided, for example, by telephone lines. The communication interface of the ICU could then be a standard telephone jack.

BRIEF DESCRIPTION OF DRAWINGS

Preferred embodiments of the invention are described below with reference to the drawings, which are described as follows.

DETAILED DESCRIPTION OF THE PREFERRED EMBODIMENTS

The ultrasonic treatment apparatus of the present invention is used for therapeutically treating injuries using ultrasound. Although the traditional emphasis has been on the treatment of musculoskeletal injuries, other injuries including venous ulcers are also contemplated. The apparatus includes a portable ultrasonic treatment composite that includes an integrated circuit unit ("ICU") that is positioned adjacent, and linked electronically, to a transducer portion. The ICU houses signal generator circuitry that provides driving signals to a transducer via the electronic link. The driving signals are enabled and disabled by internal timer circuitry. The timer is controlled by control signals from external treatment control circuitry, received via a communication interface on the ICU. In operation, the operative surface of the transducer is positioned adjacent an external skin location corresponding to the injured area. The external treatment control circuitry is used to set the timer, thus enabling the signal generator circuitry. The signal generator circuitry then creates driving signals for the transducer, which delivers therapeutic ultrasonic treatment to the external site.

Figure 1:
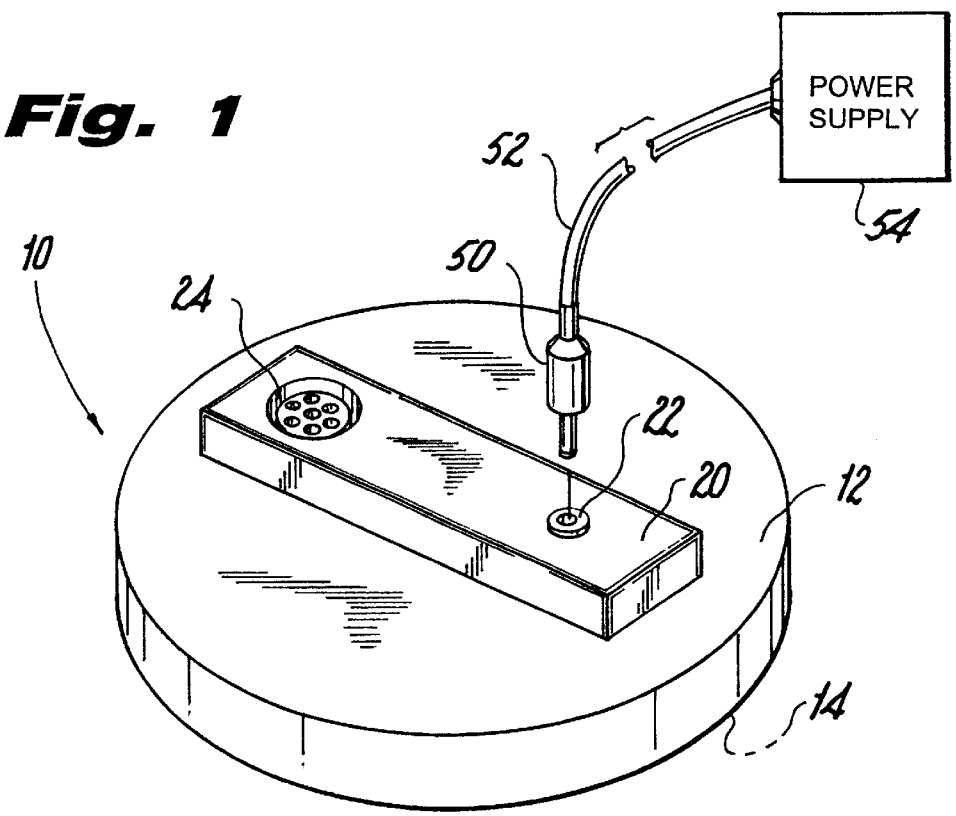
FIG. 1 is a perspective view of a portable ultrasonic treatment composite according to the present invention and an external power supply, the ultrasonic treatment composite illustrating a integrated circuit unit ("ICU") and an ultrasonic transducer.

Turning to the figures, in particular FIG. 1, the portable ultrasonic treatment composite 10 of the present invention is shown. The ultrasonic treatment composite 10 includes an ultrasonic transducer 12 coupled to an ICU 20. The piezoelectric transducer 12 has a wafer-like shape, with the ICU 20 mounted on the side opposite the operative surface 14 of the transducer 12. (The "operative surfacer" of the transducer 12 is defined as the surface from which ultrasound is emitted by the transducer 12. The "back side" of the transducer 12 is defined as the side of the transducer 12 opposite the operative surface 14.)

The ICU 20 has a first interface, shown as a jack 22, for receiving power from an external power supply 54. (Power is delivered from the power supply 54 through a lead 52 and a plug 50 that is received in jack 22.) The ICU 20 also has a second interface, also shown as a jack 24, for receiving control signals from external treatment control circuitry, described further below.

Figure 2:
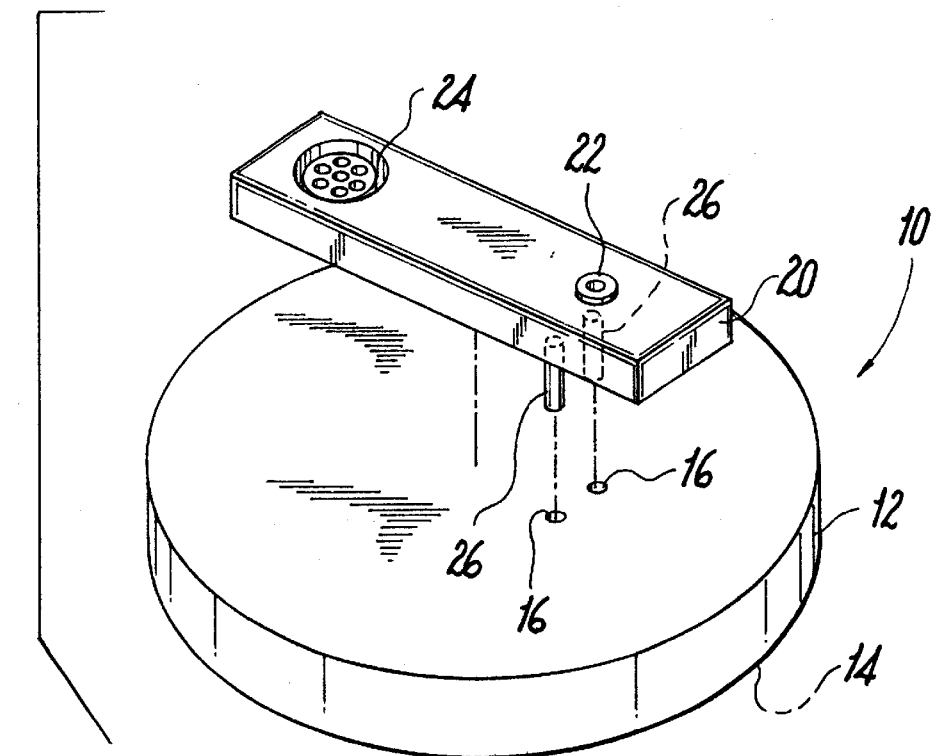
FIG. 2 is a exploded perspective view of the portable ultrasonic treatment composite of FIG. 1, with the ICU shown separated from the transducer.

Referring to FIG. 2, the transducer 12 is shown separated from the ICU 20. The surface of the ICU 20 adjacent the back side of the transducer 12 has a series of electronic pins 26 that are received in receptors 16 on the back side of the transducer 12. As described further below, this provides the electronic link for the driving signals generated by the ICU 20 and sent to the transducer 12.

Figure 3:
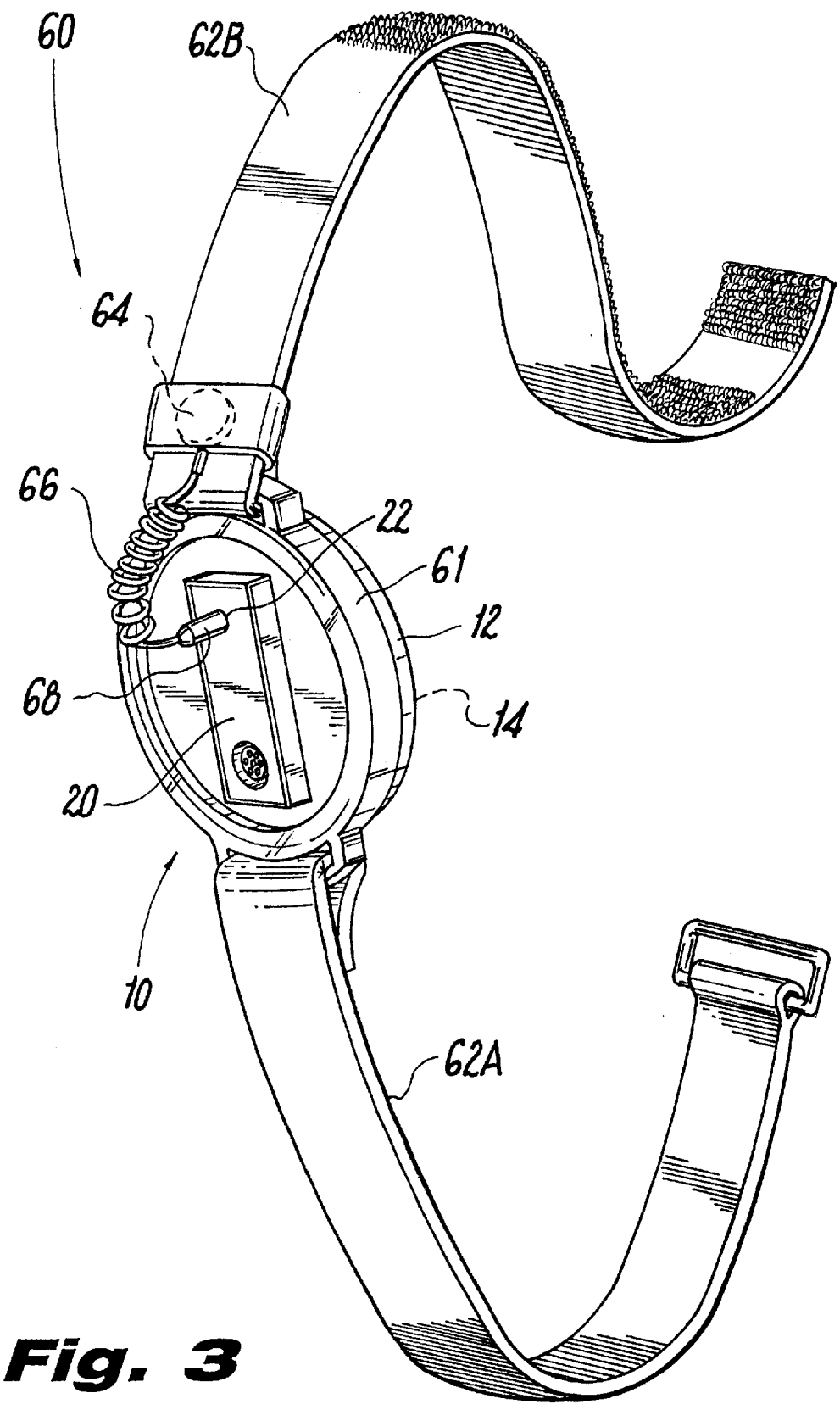
FIG. 3 is a perspective view of the portable ultrasonic treatment composite of FIGS. 1 and 2 having straps for attaching the composite adjacent an external skin location, and a battery pack integral with a strap.
Figure 4:
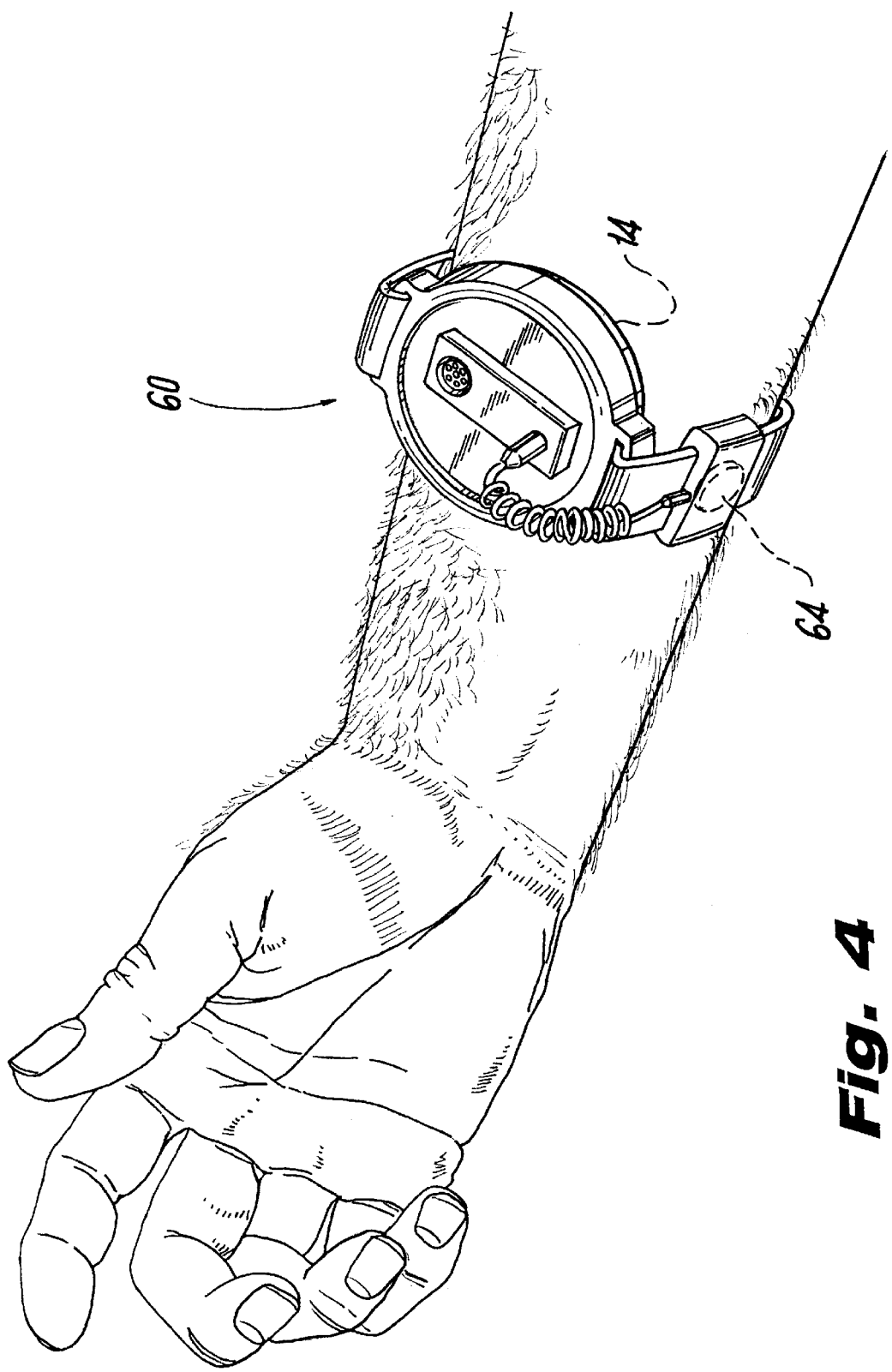
FIG. 4 is a perspective view of a patient wearing the portable ultrasonic treatment composite of FIG. 3 during treatment.

FIG. 3 shows the ultrasonic treatment composite 10 of the present invention as part of a unit 60 that may be used to position the transducer 12 adjacent an external skin location corresponding to an injury. A plastic frame 61 securely envelops the perimeter of the transducer 12. Strap segments 62A, 62B interface with frame 61, and one strap segment 62B supports a battery holder 64 for a lithium battery that supplies power to the ICU 20. (Power cord 66 connects to the battery holder 64, and plug 68 of power cord 66 is received in jack 22 of ICU 20. Other interfacing methods between the power cord 66 and the ICU 20 may be substituted, including hardwiring one end of the power cord 66 directly to the ICU 20.) FIG. 4 depicts the unit 60 of FIG. 3 attached to a patient's arm so that the operative surface 14 of the transducer 12 is adjacent an external skin location on the arm. When activated, as described below, the transducer would provide therapeutic ultrasonic treatment to the patient's arm at that location.

Figure 5:
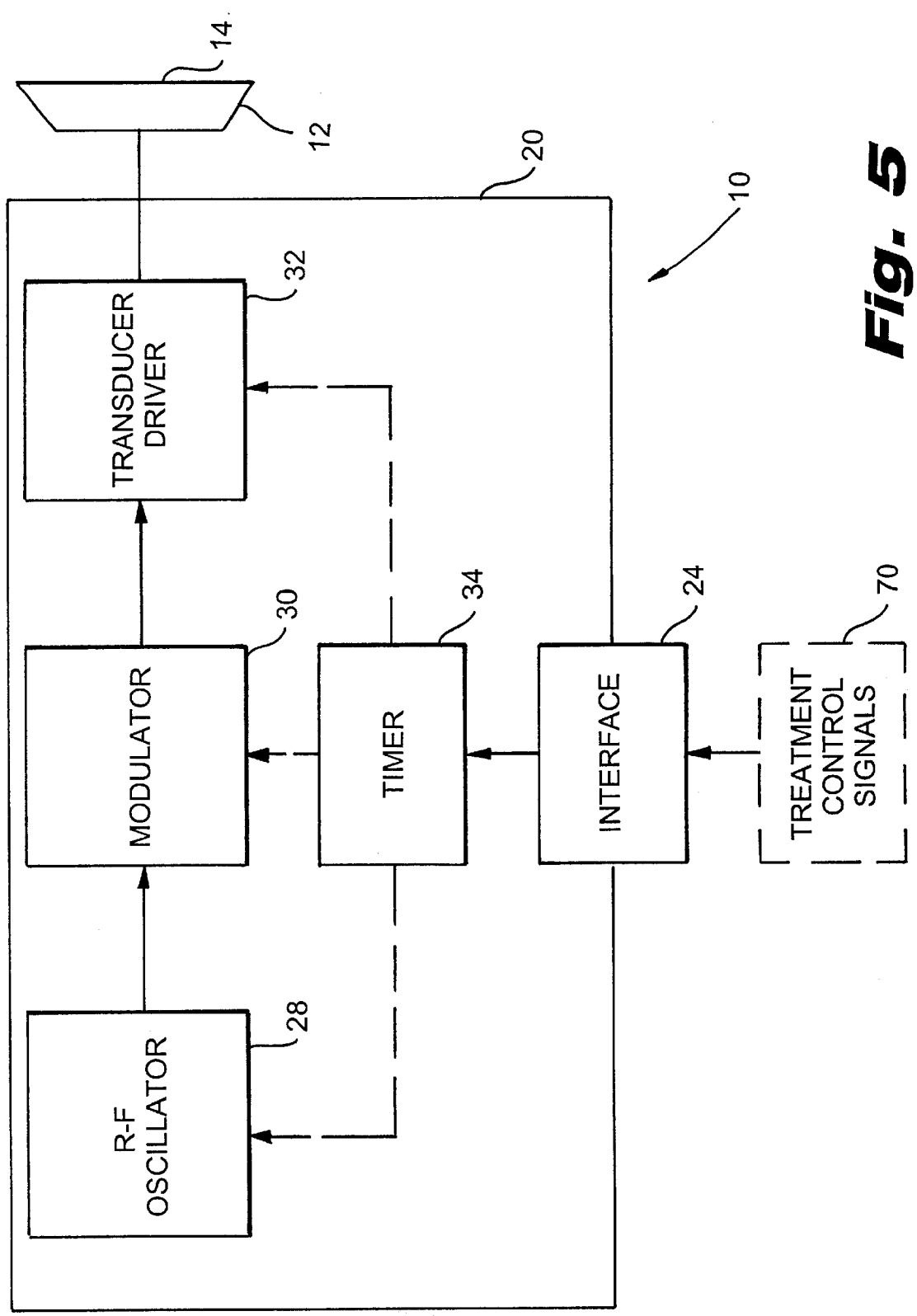
FIG. 5 is a block diagram of the circuitry of the ICU of FIGS. 1 and 2.

Referring to FIG. 5, a block diagram of one embodiment of the signal generating circuitry of the ICU 20 is shown. The signal generating circuitry includes an R-F oscillator 28 that is connected through a modulator 30 to a transducer driver 32. The transducer driver 32 excites transducer 12. (The transducer driver 32 is connected to the transducer 12 via the pins 26 and receptors 16 shown in FIG. 2) The signal generating circuitry is enabled by a timer 34. The timer 34 may, for example, be an electronic switch between the power input to the ICU 20 and one or more of its internal components, as represented by the dashed lines between the timer 34 and the R-F oscillator 28, modulator 30 and transducer driver 32. The timer 34 is set by treatment control signals 70 received from external treatment control circuitry, described further below.

As noted above, in general, the R-F oscillator 28 will generate an ultrasound carrier frequency between 250 kHz and 10 MHz. The carrier frequency is modulated by the modulator 30 with a relatively low-frequency signal (e.g. 5 Hz to 10 kHz). The modulated carrier frequency is input into the transducer driver 32, which generates driving signals for the transducer 12. The transducer 12 emits low intensity acoustic signals (e.g. less than 100 milliwatts/cm$^2$) effective in therapeutic treatment.

Figure 6:
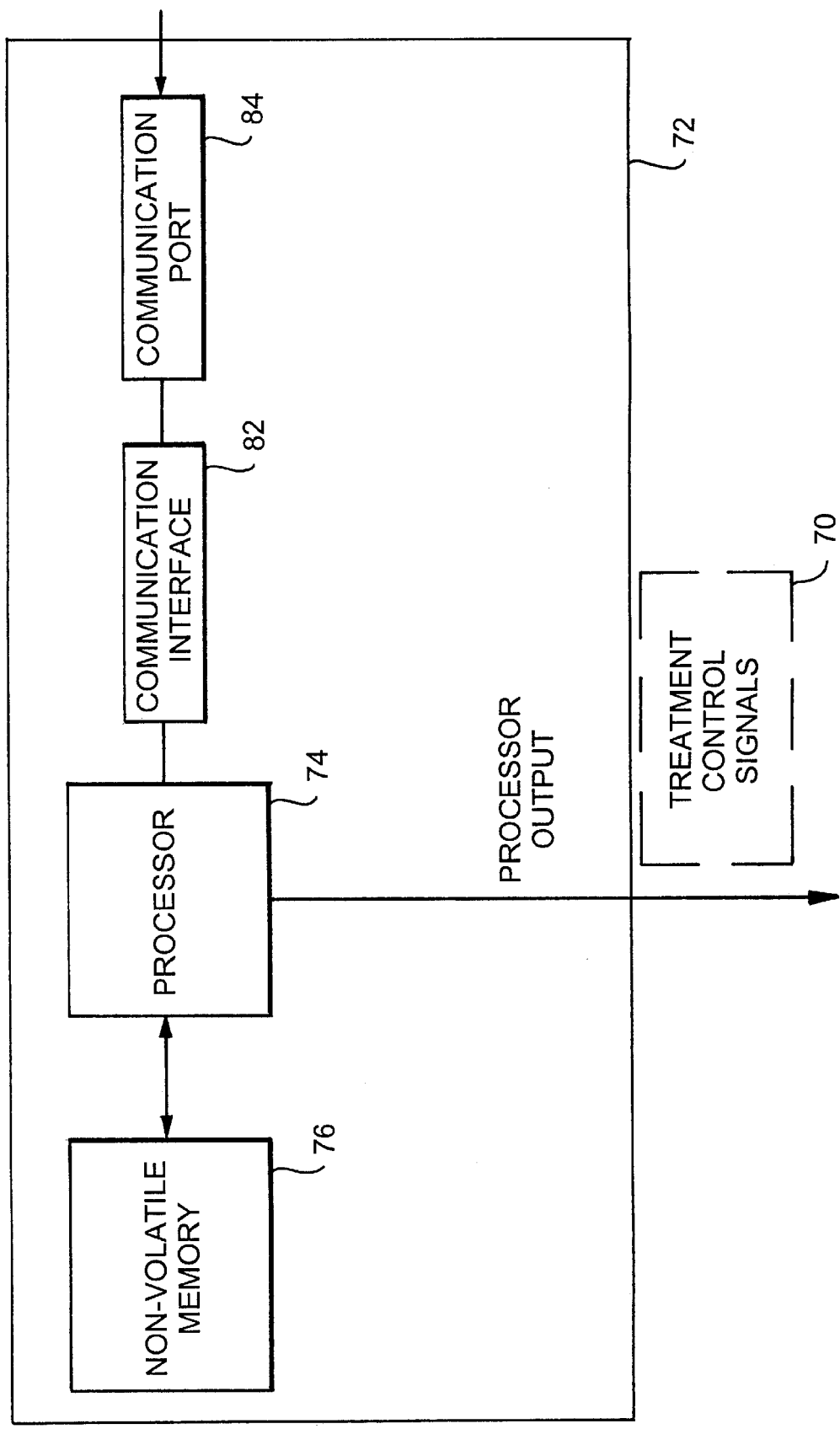
FIG. 6 is a block diagram of the circuitry of the external treatment control circuitry for the ICU of FIGS. 1 and 2.

FIG. 6 illustrates a block diagram of the external treatment control circuitry 72 that generates the treatment control signals 70 for the timer 34 of the ICU 20. The external treatment control circuitry 72 of FIG. 6 includes a processor 74 having memory 76 (e.g. RAM and ROM) with stored programs (e.g., system and application) for controlling the operation of the processor and, consequently, the ICU 20. Processor 74 may include a microprocessor, such as the Intel® 80/×86 family of microprocessors, or processor 74 may be a microcontroller having internal memory. Processor 74 is utilized to control the time of the ultrasonic treatment for a particular patient. In order to activate the ultrasonic treatment therapy, processor 74 transmits treatment control signals 70 tailored for the patient to timer 34 of ICU 20 via interface 22 (see FIG. 5. The treatment control signals 70 set timer 34 for the appropriate treatment time, which enables the signal generating circuitry of the ICU 20, as described above. When the treatment time expires, the timer disables the signal generating circuitry.

The external treatment control circuitry 72 of FIG. 6 is particularly suited for a portable control unit that is pre-programmed and assigned to each patient for activating the ultrasonic composite. Communication interface 82 is connected between communication port 84 and processor 74 and is provided to communicate with, for example, an external computer. Thus, the memory 76 may be pre-programmed prior to assignment to the patient so that the treatment times sent by the processor 74 via the treatment control signals 70 are suited for the particular patient. (Typical treatment times may range between 1 and 55 minutes, although treatments on the order of 10–20 minutes are typical.) Communication interface 82 may be a serial interface, such as an RS-232 interface, a parallel interface, or a modem.

Figure 7:
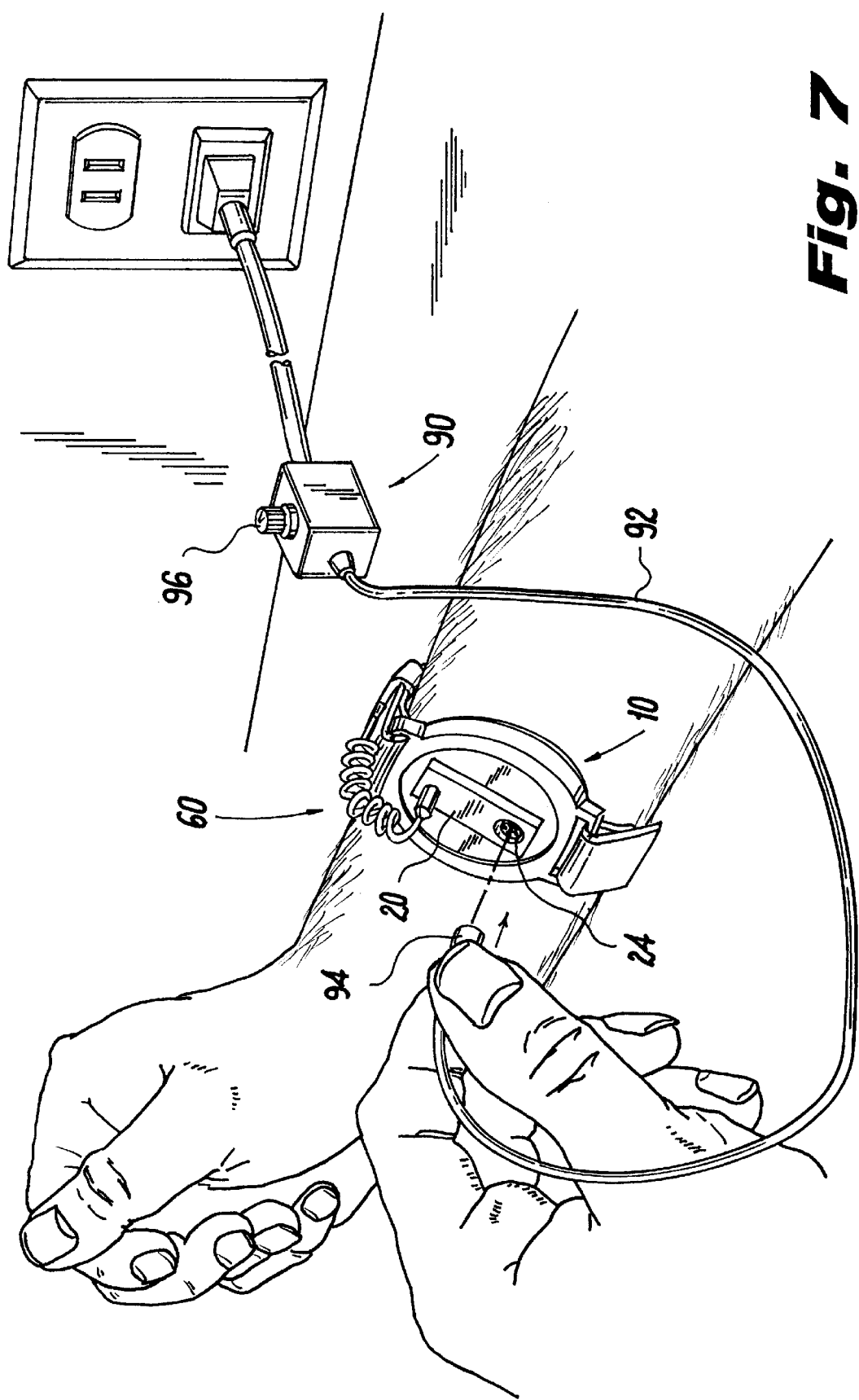
FIG. 7 is a perspective view of a patient wearing the portable ultrasonic treatment composite of FIG. 3 with a portable control unit containing external treatment control circuitry.

FIG. 7 shows a portable control unit 90 housing the external treatment control circuitry of FIG. 6, which has been pre-programmed for the therapeutic requirements of the patient shown. The control unit 90 shown activates the ultrasonic treatment composite 10 of FIGS. 1 and 2, as incorporated into the unit 60 of FIG. 3, and having the signal control circuitry of FIG. 5. To begin the ultrasonic treatment, the patient completes a control interface by connecting plug 92 of lead 92 from control unit 90 into the jack 24 on the ICU 20. The patient activates the external treatment control circuitry (shown in FIG. 6) by pressing button 96, and the processor 74 transfers the treatment control signals 70 to the timer 34 of the ICU 20 (shown in FIG. 5). As described above, the signal generator circuitry of the ICU 20 is thereby enabled for the duration set by the timer, and the prescribed ultrasonic therapy is delivered. Once unit 60 is enabled, the plug 94 may be detached, thereby allowing complete patient mobility.

Instead of assigning an individual control unit 90 to the patient for creating the treatment control signals 70 for the ICU 20, as in FIG. 7, the external treatment control circuitry may reside in a remote, centralized data processing center. The center could be linked to telephone lines and the patient could place a telephone call to access the external treatment control circuitry and activate downloading of the treatment control signals 70 to the ICU 20. After placing the call, the patient could, for example, enter an identification code via the telephone touchpad, thus identifying to the data center the memory location for the patient's data, and initiating the data processing that generates the treatment control signals 70 for that particular patient. The control interface 24 on the ICU 20 of the ultrasonic composite (see FIG. 5) may be, for example, a standard telephone jack. After entering the identification code, the patient would then disconnect the plug from the telephone, and plug it into the jack interface 24 on the composite 20. The treatment control signals 70 would then be transmitted from the remote external treatment control circuitry to activate the signal generator circuitry of the ICU 20.

Figure 8:
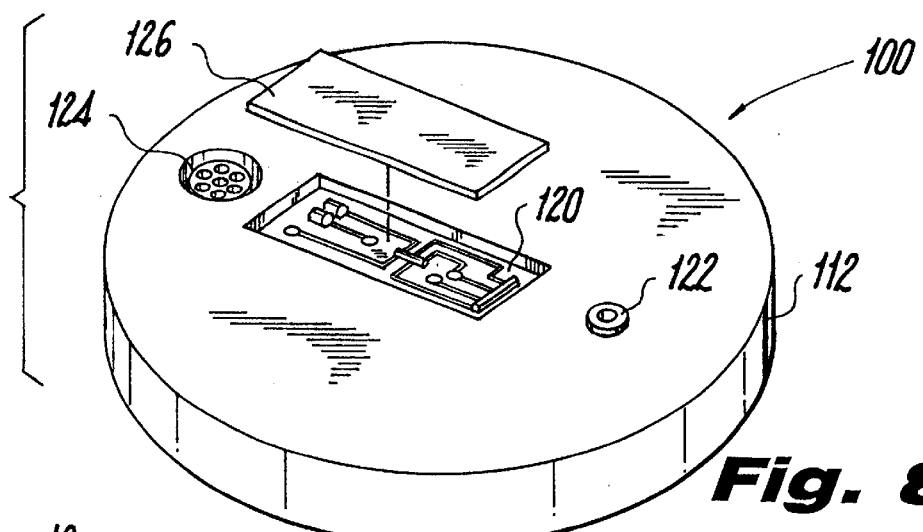
FIG. 8 is a perspective view of an alternative preferred embodiment of a portable ultrasonic treatment composite according to the present invention with the integrated circuit and ultrasonic transducer housed on the same substrate.

As noted above, the ultrasonic treatment composite is not limited to the configuration shown in FIGS. 1 and 2. In a preferred alternative embodiment, shown in FIG. 8, the back side of the ceramic piezo-electric wafer of the transducer 112 forms the substrate for the ICU 120 of the ultrasonic treatment composite 100. The signal generator circuitry of the ICU 120 may be the same as those shown in FIG. 5, but the interface between the transducer driver and the transducer would be internal to the silicon wafer. As shown in FIG. 8, the power interface 122 and the control interface 124 would also be hardwired directly between the back side of the transducer substrate and the signal generator circuitry of the ICU 120. A plastic cap 126 may be used to cover the signal generating circuitry of the ICU 120.

Figure 9:
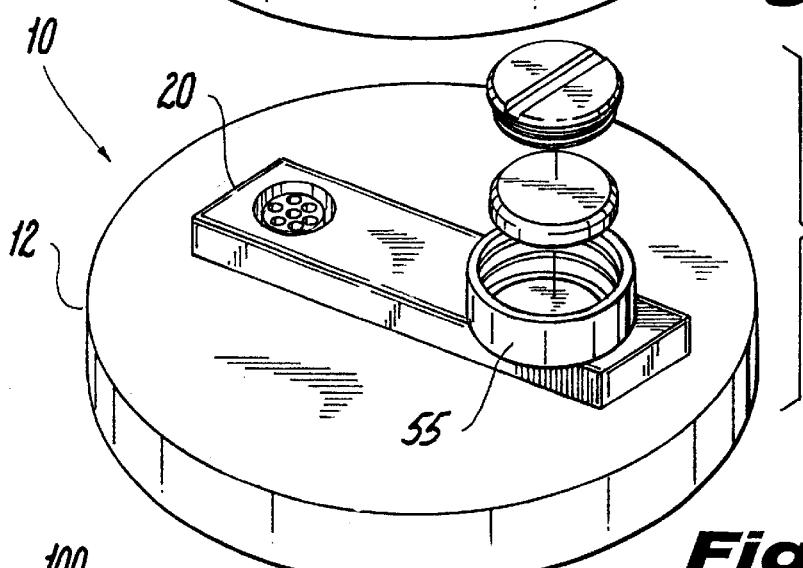
FIG. 9 is perspective view of the ultrasonic treatment composite of FIG. 1 with a battery holder mounted adjacent the integrated circuit unit.
Figure 10:
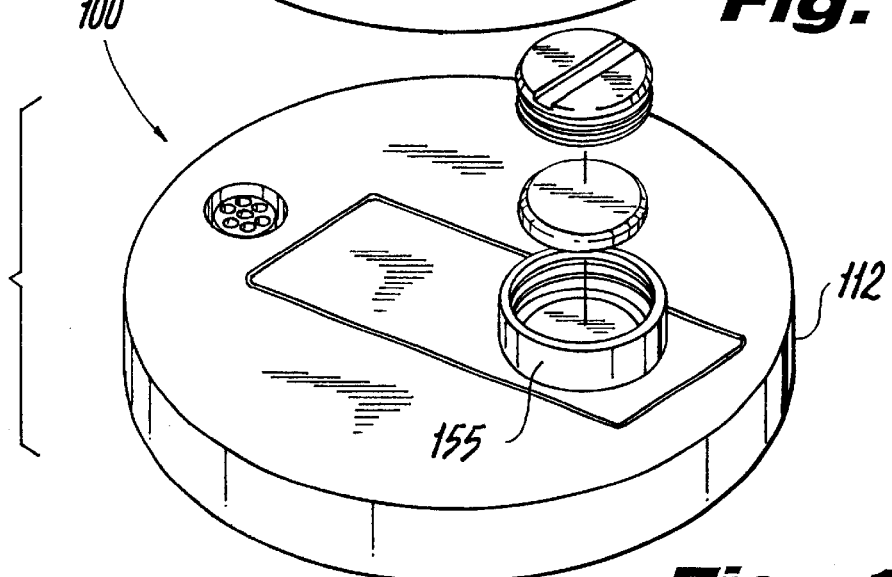
FIG. 10 is perspective view of the ultrasonic treatment composite of FIG. 8 with a battery holder mounted adjacent the integrated circuit unit.

In order to render the ultrasonic composite even more compact, the battery holder may be positioned adjacent the ICU. In FIG. 9, the composite 10 of FIGS. 1 and 2 is shown with a lithium battery holder 55 mounted adjacent the ICU 20. in this embodiment, the power interface between the battery and the signal generator circuitry of the ICU 20 is hardwired, so the power interface 22 of FIGS. 1 and 2 may be eliminated. In FIG. 10, a similar alternative embodiment of the ultrasonic treatment composite of FIG. 8 is shown with a battery holder 155 mounted adjacent the back side of the silicone wafer that houses the transducer and the ICU.

It will be understood that various modifications can be made to the various embodiments of the present invention herein disclosed without departing from its spirit and scope. For example, various shapes of the ultrasonic treatment composite, ICU and transducers are contemplated, as well as various types of construction materials. Also, various modifications may be made in the configuration of the components used to excite the ultrasonic transducer. Therefore the above description should not be construed as limiting the invention but merely as presenting preferred embodiments of the invention. Those skilled in the art will envision other modifications within the scope and spirit of the present invention as defined by the claims presented below.

What is claimed is:

1. A therapeutic ultrasonic composite comprising:
   a) a transducer;
   b) an integrated circuit unit physically disposed on the transducer, comprising
   signal generation circuitry for generating a driving signal for the transducer, a timer that interfaces with the signal generation circuitry for controlling the signal generation circuitry and capable of being activated by control signals received from an external control source, and a control interface for receiving control signals from an external control source, the signal generation circuitry, timer, and control interface housed on the integrated circuit unit;
   c) a driving interface between the signal generation circuitry and the transducer;
   wherein the signal generation circuitry is capable of generating driving signals, the interface is capable of carrying the driving signals, and the driving signals are capable of driving the transducer, which is capable of emitting therapeutic ultrasound.

2. A therapeutic ultrasonic composite as in claim 1, wherein the signal generation circuitry housed in the integrated circuit unit further comprises an R-F oscillator, a modulator and a transducer driver.

3. A therapeutic ultrasonic composite as in claim 1, wherein the timer controls a power supply to the signal generation circuitry.

4. A therapeutic ultrasonic composite as in claim 1, wherein the driving interface between the signal generation circuitry and the transducer includes electronic pins projecting from the integrated circuit unit, the electronic pins configured to be received in corresponding electronic receptors on the transducer.

5. A therapeutic ultrasonic composite as in claim 1, wherein the integrated circuit unit further comprises a power interface for receiving power for the signal generation circuitry from an external power source separate from the composite.

6. A therapeutic ultrasonic composite as in claim 1, further comprising a power supply positioned adjacent the integrated circuit unit and circuitry between the power supply and the signal generation circuitry.

7. A therapeutic ultrasonic composite as in claim 6, wherein the power supply is a battery.

8. A therapeutic ultrasonic composite as in claim 6, further comprising a means for attaching and positioning the composite with the operative surface of the transducer adjacent an external skin location.

9. The therapeutic ultrasonic composite as in claim 1, wherein the transducer comprises a piezoelectric substrate having an operative surface for emitting ultrasound and at least one nonoperative surface, and wherein the integrated circuit unit is mounted on a nonoperative surface.

10. A system for providing therapeutic ultrasonic therapy comprising:
    a) an ultrasonic treatment composite comprising a transducer, and an integrated circuit physically disposed on and interfacing electronically with the transducer, the integrated circuit comprising signal generation circuitry configured to provide driving signals to the transducer via the interface for the generation of therapeutic ultrasound, and a timer that interfaces with the signal generation circuitry for controlling the signal generation circuitry, and capable of being activated by control signals received from an external control source;
    b) external treatment control circuitry separate from the composite, the external treatment control circuitry configured to generate control signals capable of activating the timer on the integrated circuit; and
    c) control interface between the external treatment control circuitry and the integrated circuit for transmitting the control signals generated by the external treatment control circuitry to the integrated circuit.

11. A system for providing therapeutic ultrasonic therapy as in claim 10 wherein the external treatment control circuitry resides in a portable control unit.

12. A system for providing therapeutic ultrasonic therapy as in claim 11 wherein the external treatment control circuitry includes a processor and memory for storing data pertinent to an individual patient.

13. A system for providing therapeutic ultrasonic therapy as in claim 10 wherein the external treatment control circuitry resides in a centralized data processing center.

14. A system for providing therapeutic ultrasonic therapy as in claim 13 wherein the generation of the control signals by the external treatment control circuitry may be initiated by a patient at a remote location by transmission of an electronic code.

15. A system for providing therapeutic ultrasonic therapy as in claim 14 wherein the electronic code is transmitted over a telephonic connection.

16. A system for providing therapeutic ultrasonic therapy as in claim 13 wherein the control signals generated by the external treatment control circuitry are transmitted from the centralized data processing center to the integrated circuit over a telephonic connection.

17. A therapeutic ultrasonic composite comprising:
    a) a transducer formed by a portion of a piezoelectric substrate, the transducer having an operative surface for the emission of therapeutic ultrasound;
    b) an integrated circuit unit formed in an portion of the piezoelectric substrate, the integrated circuit having signal generation circuitry for generating driving signals for the transducer;
    c) a driving interface formed within the substrate between the signal generation circuitry and the transducer;
    wherein the signal generation circuitry is capable of generating driving signals, the interface is capable of carrying the driving signals, and the driving signals are capable of driving the transducer, which is capable of emitting therapeutic ultrasound at the operative surface.

18. A therapeutic ultrasonic composite as in claim 17, wherein the signal generation circuitry includes an R-F oscillator, a modulator and a transducer driver.

19. A therapeutic ultrasonic composite as in claim 17, wherein the piezo-electric substrate includes a control interface, the control interface for receiving control signals from an external control source, the control signals used to control the signal generation circuitry.

20. A therapeutic ultrasonic composite as in claim 19, wherein the integrated circuit includes a timer that interfaces with the signal generation circuitry for controlling the signal generation circuitry, the timer activated with the control signals received from the external control source.

21. A therapeutic ultrasonic composite as in claim 19, wherein the control signals from the external control source control a power supply to the signal generation circuitry.

22. A therapeutic ultrasonic composite as in claim 17, wherein the piezo-electric substrate includes a power interface for receiving power for the signal generation circuitry from an external power source separate from the composite.

23. A therapeutic ultrasonic composite as in claim 17, further comprising a power supply positioned adjacent the integrated circuit unit and hardwired electronic circuitry between the power supply and the signal generation circuitry.

* * * * *